(12) United States Patent
Zaiser et al.

(10) Patent No.: US 7,708,016 B2
(45) Date of Patent: May 4, 2010

(54) GAS CONSERVING REGULATOR

(75) Inventors: LeNoir E. Zaiser, Naples, FL (US); Kevin Confoy, Naples, FL (US)

(73) Assignee: Inovo, Inc., Naples, FL (US)

( * ) Notice: Subject to any disclaimer, the term of this patent is extended or adjusted under 35 U.S.C. 154(b) by 0 days.

(21) Appl. No.: 10/706,872

(22) Filed: Nov. 12, 2003

(65) Prior Publication Data

US 2004/0154693 A1 Aug. 12, 2004

Related U.S. Application Data

(60) Provisional application No. 60/425,834, filed on Nov. 12, 2002.

(51) Int. Cl.
*A62B 7/04* (2006.01)
*F16K 31/26* (2006.01)

(52) U.S. Cl. .............. 128/204.26; 128/204.18; 128/200.24; 128/201.28; 128/205.16; 128/205.18; 128/205.24; 128/204.27; 128/204.29; 128/205.22; 137/505.27; 137/505.28; 137/507

(58) Field of Classification Search ............ 128/204.26, 128/204.18, 200.24, 201.28, 205.16, 205.18, 128/205.24, 204.27, 204.29, 205.22; 137/505.27, 137/505.28, 507
See application file for complete search history.

(56) References Cited

U.S. PATENT DOCUMENTS

| 3,522,816 | A | * | 8/1970 | Springer | .............. 137/805 |
| 4,266,538 | A | * | 5/1981 | Ruchti | ............ 128/204.26 |
| 4,705,034 | A | * | 11/1987 | Perkins | ............ 128/204.21 |
| 5,038,774 | A | * | 8/1991 | Chabert | ............ 128/205.24 |
| 5,241,955 | A | * | 9/1993 | Dearman et al. | ....... 128/204.18 |
| 6,116,242 | A | | 9/2000 | Frye et al. | |
| 6,364,161 | B1 | | 4/2002 | Pryor | |
| 6,467,325 | B1 | | 10/2002 | Zaiser et al. | |
| 6,510,747 | B1 | | 1/2003 | Zaiser et al. | |
| 6,647,983 | B2 | * | 11/2003 | Smith et al. | ............ 128/205.24 |

* cited by examiner

*Primary Examiner*—Patricia M Bianco
*Assistant Examiner*—Nihir Patel
(74) *Attorney, Agent, or Firm*—The Johnson IP Law Firm; Rodney D. Johnson, Esq.

(57) ABSTRACT

A gas regulator includes a delivery valve assembly having a delivery outlet and a delivery valve member engageable with the delivery outlet for controlling flow of a gas from a gas source. A timing gas chamber receives gas from the gas source. Gas pressure within the timing gas chamber controls the operation of the delivery valve member. An adjustment system controls the amount of time required for the gas to fill the timing gas chamber so as to control the length of time that the delivery valve assembly is opened to conserve gas. In other embodiments, a capacity adjustment system can adjust the capacity of a gas reservoir system.

22 Claims, 4 Drawing Sheets

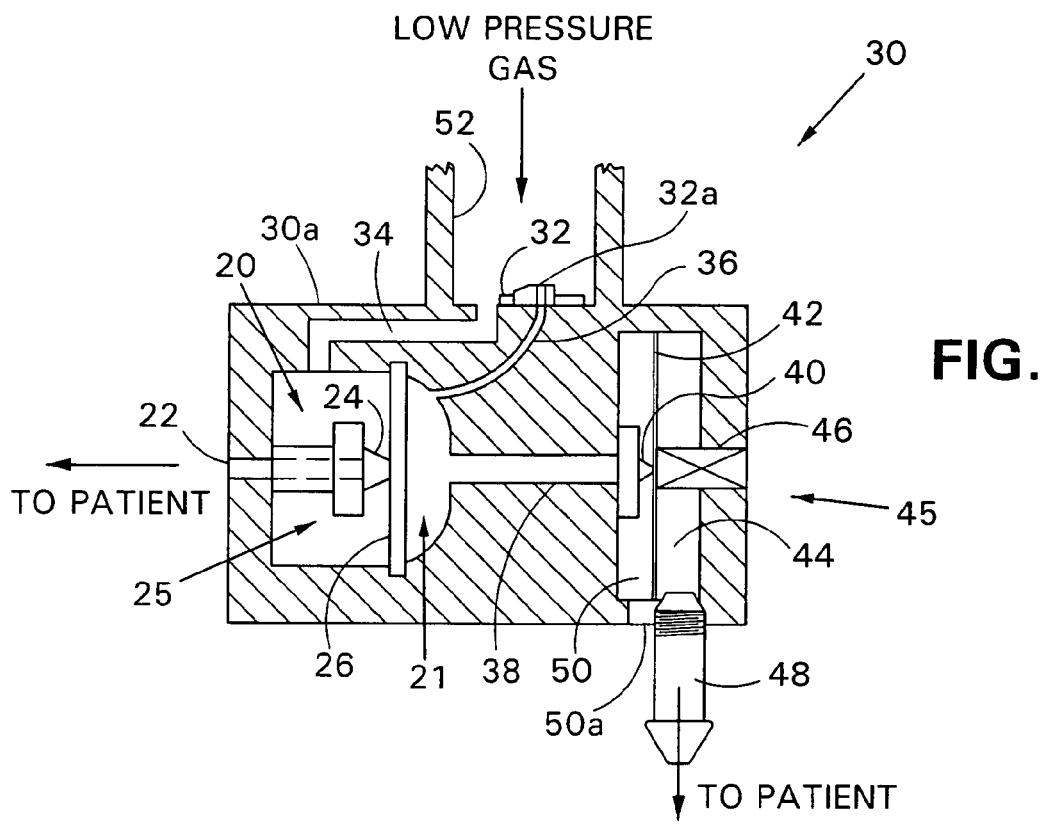
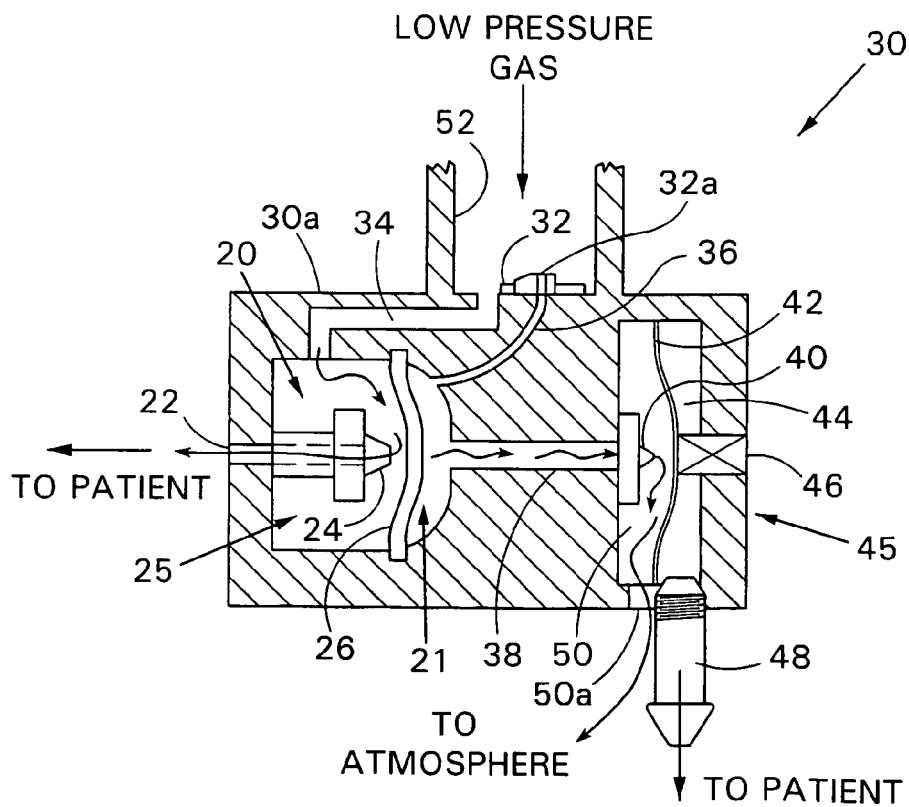

GAS CONSERVING REGULATOR

RELATED APPLICATION

This application claims the benefit of U.S. Provisional Application No. 60/425,834, filed Nov. 12, 2002. The entire teachings of the above application are incorporated herein by reference.

BACKGROUND

Gas-conserving regulators include oxygen regulators, which are used to supply a patient with a regulated flow of oxygen. The oxygen is supplied by a source of compressed oxygen, such as from a supply tank, which has its pressure reduced to a low pressure (e.g., 22 PSI) for delivery to the patient. Typical oxygen regulators employ a back-pressure piston to supply a continuous flow of that low pressure oxygen to the patient. Much of that oxygen is wasted because it is not inhaled by the patient.

To reduce the amount of wasted oxygen, oxygen-conserving regulators have been developed. These regulators tend to limit the oxygen flow to periods of inhalation. The oxygen flow can be controlled electronically or pneumatically.

In pneumatic conserving regulators, a reservoir coupled to the oxygen source holds a supply of oxygen for delivery to the patient. Delivery of the oxygen is controlled by a slave diaphragm that separates the reservoir from a timing gas chamber. The slave diaphragm seals the opening to a delivery nozzle when the patient is not inhaling and releases the seal from the nozzle opening when the patient inhales. The slave diaphragm is made from a flexible material and is generally pressurized toward the closed position. Operation of the slave diaphragm is controlled by a pilot diaphragm, which is coupled to the patient. When the patient inhales, the pilot diaphragm lifts off an orifice pneumatically connected to the timing gas chamber. The oxygen in the timing gas chamber is then expelled, creating a pressure drop sufficient to allow the slave diaphragm to move away from the slave nozzle, thus allowing flow to the patient.

In a dual-lumen conserver (i.e., demand conserver), when the patient stops inhaling—causing the pilot diaphragm to close—the timing chamber builds back to operating pressure (e.g., 22 PSI) almost immediately. Consequently, when the pilot diaphragm shuts against the pilot nozzle, flow to the patient stops. This is usually done by having a preset timing flow between 100 cc and 350 cc per minute, depending on the design of the device. The need to stop flow as soon as the pilot diaphragm closes is because, in a demand conserver, the pilot diaphragm stays open as long as the patient inhales. The dual-lumen design of such conservers allows the unit to be sensitive enough to sense the vacuum caused by inhalation.

A single-lumen conserver does not have that sensitivity, because as soon as the pilot diaphragm opens, the flow of oxygen to the patient overwhelms the device's ability to sense the vacuum caused by the patient during inhalation. In these devices, oxygen is delivered to the patient for an interval of time.

SUMMARY

Embodiments of the present invention include a gas regulator that can deliver sufficient medical gas to a patient in a manner that conserves more gas than prior art oxygen-conserving regulators. In addition, medical gas can be more efficiently delivered to the patient. In typical applications, the medical gas is oxygen.

A particular gas regulator can include a delivery valve assembly having a delivery outlet and a delivery valve member engageable with the delivery outlet for controlling flow of the gas. Gas pressure within a timing gas chamber can control the operation of the delivery valve member. A user adjustment system can control the amount of time required for the gas to sufficiently fill the timing gas chamber so as to control the length of time that the delivery valve assembly is opened.

In one embodiment, the user adjustment system can include an orifice member having more than one orifice, each of a different size, which can be selectively positioned for selecting the flow rate of the gas into the timing gas chamber. In another embodiment, a single slot having a variable width along its length is employed by placing a selectable portion of the slot in line with a passage to the timing gas chamber.

In yet another embodiment, the gas regulator can have an adjustment system that can be user adjustable and/or factory adjustable and can include a volume adjustment device for adjusting the volume of the timing gas chamber. The volume adjustment device can include an adjustable piston.

A particular embodiment of the present invention can also provide a gas regulator including a gas reservoir system. The gas reservoir system has a gas containing capacity. A capacity adjustment system can adjust the capacity of the gas reservoir system. A delivery valve assembly having a delivery outlet and a delivery valve member that is engageable with the delivery outlet controls the flow of gas from the gas reservoir system.

The gas reservoir system can include a plurality of reservoirs. The capacity adjustment system allows selected reservoirs to be connectable in communication with each other for selecting the capacity of the gas reservoir system. The capacity adjustment system can include a moveable plate having a series of orifices therethrough. The capacity of the gas reservoir system can be selected by selecting the position of the moveable plate. A tail flow can pass through the selected reservoirs. In addition, a continuous flow circuit that does not pass through the reservoirs can be selected to provide additional flow to the tail flow.

BRIEF DESCRIPTION OF THE DRAWINGS

The foregoing and other objects, features and advantages of the invention will be apparent from the following more particular description of embodiments of the invention, as illustrated in the accompanying drawings in which like reference characters refer to the same parts throughout the different views. The drawings are not necessarily to scale, emphasis instead being placed upon illustrating the principles of the invention. Furthermore, it is understood that O-rings would commonly be used for sealing purposes, but are not generally shown for clarity.

FIG. 1 is a partial side-sectional schematic of a particular embodiment of a gas conserving regulator in its rest position.

FIG. 2 is a partial side-sectional schematic of the regulator of FIG. 1 depicted during inhalation of the patient.

DETAILED DESCRIPTION

Figure 3:
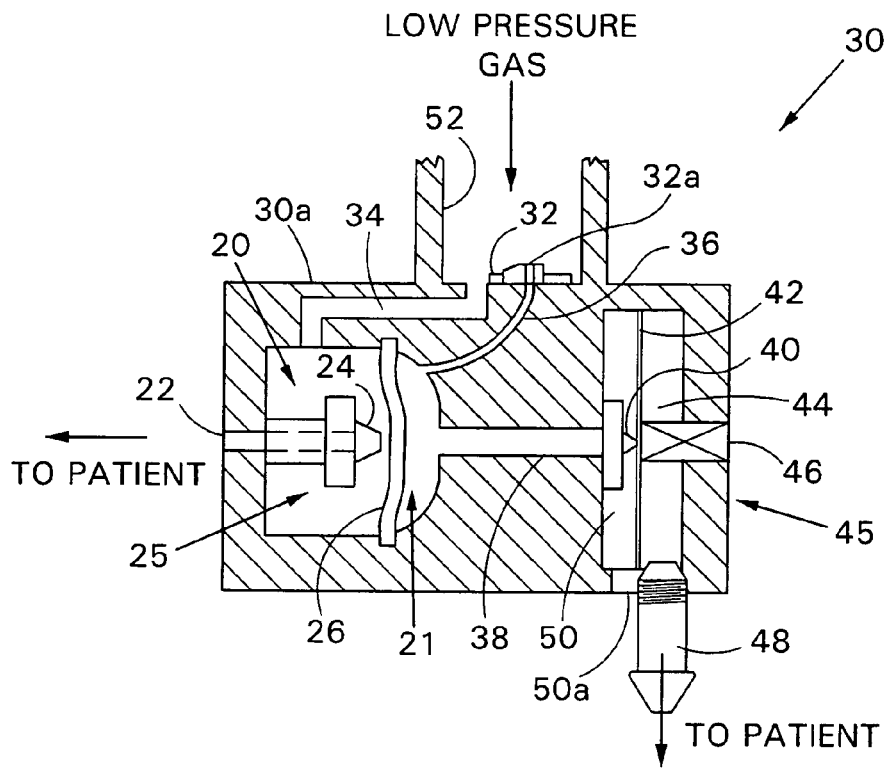
FIG. 3 is a partial side-sectional schematic of the regulator of FIG. 1 depicted at the end of inhalation of the patient.

Some examples of oxygen-conserving regulators are described in U.S. Pat. Nos. 6,364,161 to Pryor and 6,116,242 to Frye et al. Another embodiment is described in U.S. application Ser. No. 10/666,115 entitled "Differential Pressure Valve Employing Near-Balanced Pressure" by LeNoir E. Zaiser, which was filed on Sep. 19, 2003. The teachings of these patents and application are incorporated herein by reference in their entirety.

In typical prior art oxygen-conserving regulators, the inhaling patient receives an initial burst of oxygen from the reservoir, often followed by a steady flow of oxygen at the regulator's flow rate while inhalation continues or until delivery is stopped. The initial volume of gas delivered to the patient at inspiration is equal to the volume of the reservoir multiplied by the pressure of the gas in the reservoir. The volume of gas delivered can therefore be adjusted by adjusting the pressure in the reservoir.

The initial burst of delivered gas can be varied by varying the volume of the gas delivery reservoir. This can be accomplished by offering regulators with different sized gas delivery reservoirs, or by providing a gas delivery reservoir with an adjustable volume, for example, by an adjustable piston.

FIG. 1 is a partial side-sectional schematic of a particular embodiment of a gas conserving regulator in its rest position. In a typical application, oxygen gas is provided from a high-pressure supply tank. The regulator 30 can include a pressure reducing arrangement within the housing 30a, for reducing the gas pressure received from the supply tank to an operation pressure, such as about 22 psi, within a low pressure chamber 52. A suitable pressure reducing arrangement includes a restricted orifice (not shown) and a back pressure piston (not shown), as are known in the art. A gas reservoir or bolus 20 is connected to the low pressure chamber 52 through a supply passage 34.

The flow of gas from the gas reservoir 20 is controlled by a slave or delivery valve assembly 25 having a slave delivery diaphragm or valve member 26, which is engageable with a slave nozzle 24 of a delivery outlet or passage 22 to control the flow of gas through the delivery outlet 22. The delivery outlet 22 is connected to the breathing area of the patient (the nose and/or mouth) via tubing to supply the gas to the patient. The slave diaphragm 26 is controlled by the pressure within a timing gas chamber 21, which is located on the side of a slave diaphragm 26 opposite to the slave nozzle 24. The timing gas chamber 21 is in turn, controlled by a pilot valve assembly 45, which is in communication with the timing gas chamber 21 by a pilot outlet or passage 38. The timing gas chamber 21 is filled with gas from the low pressure chamber 52 through an orifice 32a in an orifice member 32 and a fill passage 36.

The pilot valve assembly 45 includes a pilot diaphragm or valve member 42, which is engageable with the pilot nozzle 40 of the pilot outlet 38 for controlling the flow of gas from the timing gas chamber 21 to the atmosphere via a vent chamber 50 and a vent outlet 50a.

The pilot diaphragm 42 is normally biased against the pilot nozzle 40 such as by a spring 46, to normally close the pilot valve assembly 45. The spring acts against the small force exerted by the pressure within the pilot nozzle 40. The pilot diaphragm 42 is controlled by the pressure within a sensing chamber 44, which is located on the side of the pilot diaphragm 42 that is opposite to the pilot nozzle 40. A fitting 48 is connected in communication with the sensing chamber 44 to which tubing is connected to the patient breathing area so that inhalation of the patient's breathing can affect the pressure within the sensing chamber 44.

Both the slave diaphragm 26 and the pilot diaphragm 42 are fixed and sealed at the outer periphery within the housing 30a. The slave diaphragm 26 and the pilot diaphragm 42 are operated by the relative gas pressures on opposite sides of the diaphragms. Because the diaphragms are flexible, they can move to lift off the respective nozzles 26, due to changes in pressure.

In operation, when at rest or when the patient is between breaths, the pilot valve assembly 45 is in the closed or sealed position, with the pilot diaphragm 42 being held or forced against the pilot nozzle 40 by the spring 46 and the gas pressure (at atmosphere) within the sensing chamber 44. This prevents gas that has entered the gas timing chamber 21 via the orifice 32a and the fill passage 36 from exiting the gas timing chamber 21.

The gas pressure within the gas timing chamber 21, in turn, causes the slave valve assembly 25 to be closed or sealed, with the slave diaphragm 26 being held or forced against the slave nozzle 24 by this gas pressure. As a result, gas that has entered the gas reservoir 20 from the low pressure chamber 52 via the supply passage 34 cannot exit the gas reservoir 20.

FIG. 2 is a partial side-sectional schematic of the regulator of FIG. 1 depicted during inhalation of the patient. As shown, with the sensing chamber 44 being connected to the breathing area of the patient, inhalation by the patient causes a gas pressure drop within the sensing chamber 44. The reduction in air pressure in the sensing chamber 44 creates a pressure differential on the pilot diaphragm 42, which allows the pilot diaphragm 42 to move away from the pilot nozzle 40. That movement opens the pilot valve assembly 45 and releases gas from the timing gas chamber 21 to the atmosphere through the pilot outlet passage 38, the pilot nozzle 40, the vent chamber 50 and the vent outlet 50a, as shown by the arrows.

In addition, the release of gas within the timing gas chamber 21 creates a pressure differential on the slave diaphragm 26, which allows the slave diaphragm 26 to move away from the slave nozzle 24 and thereby opening the slave valve assembly 25. As a result, gas within the gas reservoir 20 is allowed to exit through the delivery outlet 22 for delivery to the patient. Additional gas flowing into the gas reservoir 20 through the supply passage 34 can be delivered to the patient for as long as the slave valve assembly 25 remains open, as shown by the arrows.

FIG. 3 is a partial side-sectional schematic of the regulator of FIG. 1 depicted at the end of inhalation of the patient. As shown, when the patient stops inhaling, the pressure within the sensing chamber 44 rises back to atmospheric pressure, thereby (with the help of the pilot spring 46) causing the pilot diaphragm 42 to engage the pilot nozzle 40 and close the pilot valve assembly 45. Consequently, gas is no longer allowed to escape from the timing gas chamber 21 and the timing gas chamber 21 becomes filled with gas from the low pressure chamber 52 via the orifice 32a in the orifice member 32 and the fill passage 36.

In one particular embodiment, the orifice member 32 has a series of orifices 32a of different sizes which can be selectively positioned in communication with the fill passage 36. As a result, the flow rate into the timing gas chamber 21 can be chosen by selecting the desired orifice 32a in the orifice member 32 and moving the orifice member 32 into the proper position for aligning the desired orifice 32a in alignment with the fill passage 36. In some embodiments, orifices 32a having flow rates ranging between 35 cc and 350 cc can be selected.

For example, the orifice member 32 can be rotatable plate or disc, or alternatively, a sliding plate that is translated linearly.

Selection of the size of the orifice 32a allows selection of the length of time that it takes the timing gas chamber 21 to be filled. In turn, the length of the time required for filling the timing gas chamber 21 determines the length of time that the slave valve assembly 25 remains open and the length of time that gas continues to be delivered to the patient after the pilot diaphragm 42 closes.

In another particular embodiment, the orifice member 32 includes an annular or linear slot instead of a plurality of orifices 32a. The slot would have a variable width along its length. As the orifice member 32 is moved, the portion of the slot in communication with the fill passage 36 has a changing area, thereby adjusting the flow rate through the fill passage 36 in a continuously variable manner.

Once the timing gas chamber 21 becomes adequately pressurized, the gas pressure therein forces the slave diaphragm 26 against the slave nozzle 24, thereby closing the slave valve assembly 25 and stopping the flow of gas from the gas reservoir 20 to the patient, such as depicted in FIG. 1. The regulator 30 is then ready for the patient's next breath.

By having a series of orifices 32a with different sizes in the regulator 30, the rate at which the timing gas chamber 21 repressurizes can be varied so that the volume of gas delivered to the patient can be varied. Consequently, the amount of delivered gas can be selected to suit individual patient's requirements, thereby reducing the amount of waste. The orifice member 32 provides an adjustment that is in addition to setting the gas pressure entering the timing gas chamber 21 and is typically adjustable by the user, but also can be adjusted at the factory.

Figure 4:
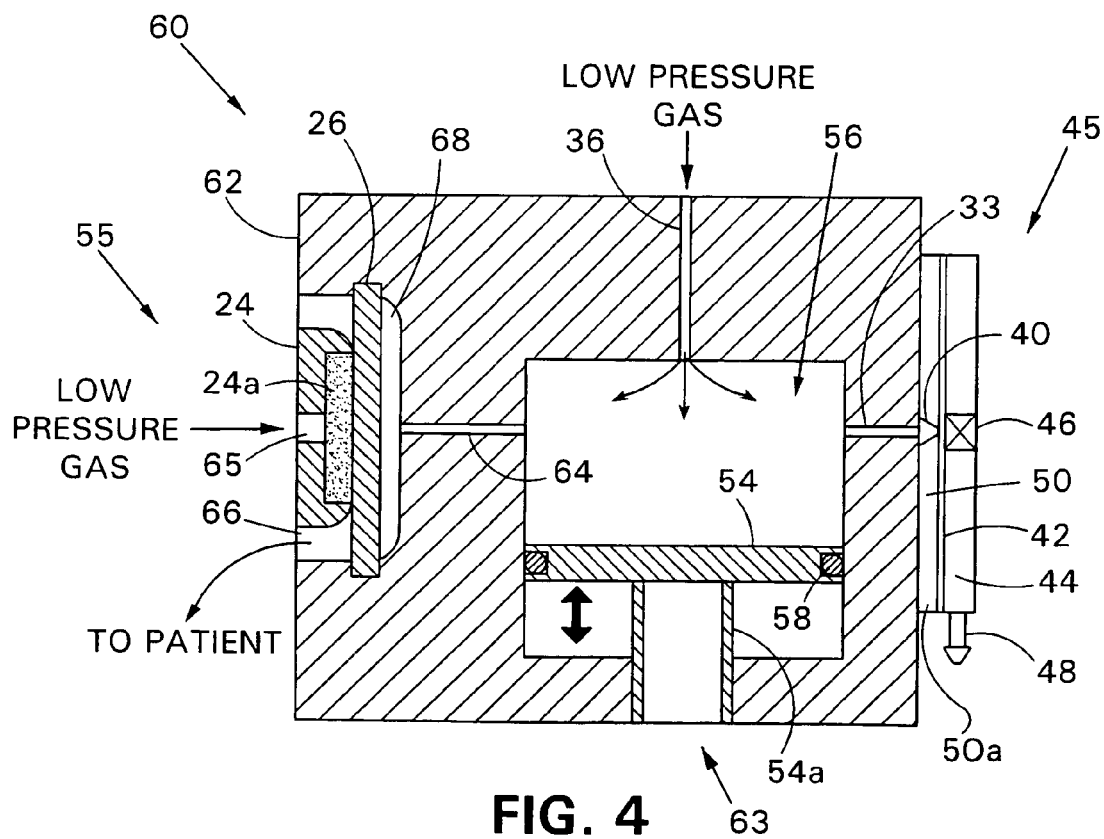
FIG. 4 is a partial side-sectional schematic of a particular adjustable timing gas chamber.

FIG. 4 is a partial side-sectional schematic of a particular adjustable timing gas chamber. Depicted is a gas conserving regulator 60 that differs from the regulator 30 (FIGS. 1-3) in that the housing 62 of the regulator 60 includes a timing gas chamber 56 having a volume or capacity that is adjustable. This regulator 60 can be used with a single lumen.

In the embodiment shown, the volume of the timing gas chamber 56 can be varied by a volume adjusting device 63, including an adjustable piston 54 moveably positioned within the timing gas chamber 56. The piston 54 includes a gas tight seal 58, such as an O-ring, for preventing the escape of gas around the piston 54. A piston rod 54a extends through the housing 62 for adjustment by an adjustment mechanism, such as an adjustment screw or a slide mechanism (not shown). The piston 54 can be adjusted at the assembly of the regulator 60 or can be adjusted by the user.

The timing gas chamber 56 is in communication with the slave or delivery valve assembly 55 through a passage 64 and a recess 68. The slave valve assembly 55 includes a nozzle 24 with a filter 24a which engages the slave delivery diaphragm or valve member 26. The slave diaphragm 26 is pressed against the slave nozzle 24 with a force of approximately the gas pressure within the recess 68 multiplied by the exposed surface area of the slave diaphragm 26. The recess 68 provides sufficient space for the slave diaphragm 26 to lift off or move away from the slave nozzle 24.

Low pressure gas, for example at 20 psi, for delivery to the patient, enters the slave nozzle 24 through an inlet 65. The inlet 65 can be connected to a gas reservoir 20 or low pressure chamber 52 (FIGS. 1-3). Gas that is delivered to the patient exits the slave valve assembly 55 through a passage 66.

In operation, the pilot valve assembly 45 is typically opened in the same manner as in the regulator 30 (FIGS. 1-3) when the patient inhales, whereby gas within timing gas chamber 56 is allowed to escape to atmosphere or to the patient through the vent outlet 50a. This in turn causes the slave diaphragm 26 to bow into the recess 68 away from the slave nozzle 24 to open the slave valve assembly 55, which allows gas to pass from the passage 65 to the passage 66 for delivery to the patient. As the gas begins to flow to the patient, the pilot valve assembly 45 closes and the timing gas chamber 56 begins to repressurize.

The volume of the timing gas chamber 56 is selected by adjusting the position of the piston 54. Typically, gas entering the gas chamber 56 through the fill passage 36 passes through a fixed orifice so that the selection of the volume of the gas chamber 56 determines the amount of length of time required to repressurize the gas chamber 56. This in turn will determine the length of time that the slave valve assembly 55 can remain open and, therefore, the volume or amount of gas that is delivered to the patient.

The volume within the timing gas chamber 56 can be adjusted, for example but not limited to between 0-1 cc. The flow rate into the gas chamber 56 is typically lower than prior art demand conservers, for example about 60 cc/min.

Once the timing gas chamber 56 is suitably filled, the gas pressure then forces the slave diaphragm 26 back against the slave nozzle 24, thereby closing the slave valve assembly 55 and ending the gas delivery to the patient. The adjustable volume in the timing gas chamber 56 provides timing that is not affected by fluctuations in the system pressure or in the volume of gas that flows through the fill passage 36. Regardless of the operating pressure, the piston 54 can be adjusted to achieve the timing required.

The direct ratio of the timing gas chamber's 56 volume to the timing of the regulator 60 lends itself to embodiments that eliminate the need for various flow rates. Prior art pneumatic single-lumen conservers are typically designed to provide oxygen to the patient based on providing the prescribed flow rate over a fixed amount of time. For example, noting that one second is the typical length of time that a patient inhales, in the prior art, a patient with a prescription of 1 LPM would receive bolus plus a flow at a rate of 1 LPM for 1 second. If the patient has a prescription for 2 LPM, the device delivers the same bolus plus a flow rate of 2 LPM for 1 second.

In contrast to such prior art delivery systems, the regulator 60 can deliver the required volume by varying the time that the slave diaphragm 26 remains open. For example, an equivalent volume of gas for 1 LPM would be delivered by the slave diaphragm 26 staying open for only ⅙ of a second, or 2 LPM by staying open ⅓ of a second. The patient could adjust the piston 54 with a knob on the unit. The regulator 60 can be used to emulate electronic conservers that deliver lower volumes of oxygen, but in a very short time.

The regulator 60 provides increased conservation by operating under the theory that most of the therapeutic oxygen is delivered to the patient at the start of inhalation, and most oxygen delivered near the end of inhalation never makes it into the lungs. Typically, regulators 30 and 60 of FIGS. 1-4 are suitable for single lumen use but can be used with dual or double lumens.

Figure 5:
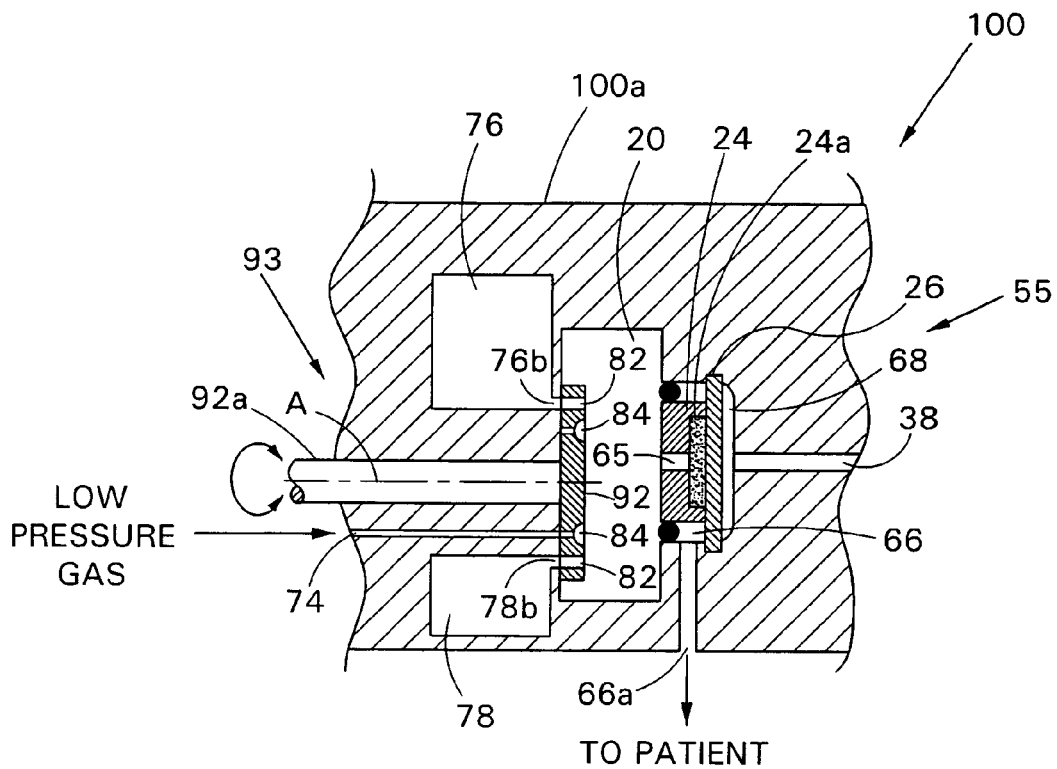
FIG. 5 is a partial side-sectional schematic of a gas conserving regulator having a variable delivery volume.

FIG. 5 is a partial side-sectional schematic of a gas conserving regulator having a variable delivery volume. As shown, the gas conserving regulator 100 has a slave or delivery valve assembly 55, which is controlled by a pilot valve assembly 45, such as in the regulator 60 (FIG. 4), but has a timing gas chamber that can have a fixed fill time.

The housing 100a of the regulator 100 includes a gas reservoir 20 serving as a common bolus chamber, as well as a series of auxiliary bolus chambers 76, 78. Although only two auxiliary bolus chambers 76, 78 are shown, embodiments of the regulator 100 can have one or more auxiliary bolus chambers. A particular embodiment includes five auxiliary bolus chambers. The auxiliary bolus chambers 76, 78 are shown as being of different volumes, but can be the same size or any suitable combination of sizes. When multiple auxiliary bolus chambers are employed, the chambers are typically arranged about a common axis A. Further description of FIG. 5 will discuss only chambers 76 and 78 because only those chambers are visible.

Low pressure gas is delivered to the gas reservoir 20 through a supply passage 74 and through an orifice or opening 84 of a selector plate 92 of a selector device 93. The selector plate 92 has a series of inner orifices or openings 84 for alignment with the supply passage 74 and a series of outer orifices or openings 82 for selective alignment with the respective openings 76b, 78b of the auxiliary bolus chambers 76, 78. The selector plate 92 is rotatably positioned along axis A and is attached to a shaft 92a which can be manually rotated by the user, for example, by a knob. By rotating the selector plate 92 into the desired position with respect to the location of the openings 82, one or both of the auxiliary bolus chambers 76, 78 can either be isolated from the common bolus chamber 20, or connected in communication with the common bolus chamber 20. The orifices 84 can be the same size or can have different sizes for different flow rates.

In operation, with the selector plate 92 positioned as shown in FIG. 5, both auxiliary bolus chambers 76, 78 are in communication with the common bolus chamber 20, so that the gas entering the common bolus chamber 20 through the supply passage 74 and the orifice 84 also enters the first bolus chamber 76 through the openings 82 and 76b, and the second bolus chamber 78 through the openings 82 and 78b. Consequently, when the slave valve assembly 55 is opened, gas from the common bolus chamber 20 and the bolus chambers 76, 78, known as bolus gas, is delivered to the patient via the passage 66 and the outlet 66a.

Figure 6:
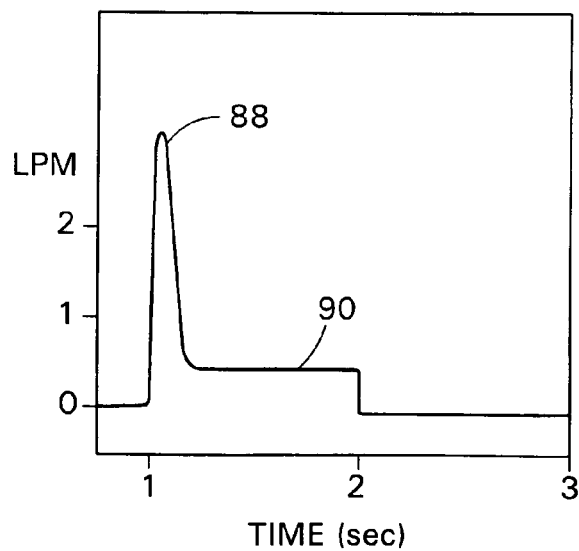
FIG. 6 is a graph of an example flow rate versus time for the regulator of FIG. 5.

FIG. 6 is a graph of an example flow rate versus time for the regulator of FIG. 5. The bolus gas is depicted as the large peak 88. The lower constant peak 90 is the tail flow gas, which is provided by the gas flowing into the gas reservoir 20 from the supply passage 74. By moving the selector plate 92 into different positions, the peak 88 of the bolus gas can be raised or increased by connecting more bolus chambers to the gas reservoir 20, or lowered or decreased by blocking or isolating bolus chambers from the gas reservoir 20. In addition, the level of the tail flow gas 90 can be raised or increased by positioning a larger sized orifice 84 in line with the supply passage 74, or lowered or decreased by positioning a smaller sized orifice 84 in line with the supply passage 74.

Typically, the fixed volume of bolus gas is delivered to the patient at the start of each breath. The volume commonly selected ranges from 3 ml to 30 ml or more, but other suitable ranges can be employed. For the remainder of the inhalation, the gas is delivered at a lower but fixed rate in the tail flow. The tail flow is whatever it takes to reach the expected delivery volume of the selected flow rate.

Typically, the selector knob attached to the shaft 92a can indicate a total gas flow. The tail gas flow rate that is delivered is calculated to complement the bolus gas for delivering a total fixed volume of gas over the breath. When inhalation ceases, the tail flow ceases and the regulator 100 is reset to be ready for the next breath.

It is believed that the therapeutic value of oxygen comes in the initial phases, first 600 milliseconds (ms), of the inhalation, even though a breath typically lasts about a second. Therefore, the final 400 ms of oxygen delivered by the device is wasted, because the oxygen never reaches the patient's lungs. Use of a lower flowing tail flow minimizes this loss and conserves gas.

To maximize the amount of oxygen that reaches the patient within the first 600 milliseconds, the bolus is as large as possible without exceeding the amount of oxygen that would be delivered to the patient with a continuous flow regulator. For example, it is generally understood that at a constant flow of 1 LPM, about 10 ml of oxygen is delivered to the patient's lungs per breath for a constant flow with no bolus. Therefore, the bolus delivered at a 1 LPM setting should not exceed 10 ml, and in reality should be lower than that because some tail flow is required. Higher constant flow rate would require higher volumes of oxygen delivered to the patient. Therefore, using a multiple bolus system, where each bolus can be of the same or different volume and used either singly or in conjunction with each other, allows flexibility in delivering the proper bolus to the patient while minimizing tail flow. The regulator 100 can conserve about 67% of oxygen, resulting in about a 3:1 conserving ratio.

Figure 7:
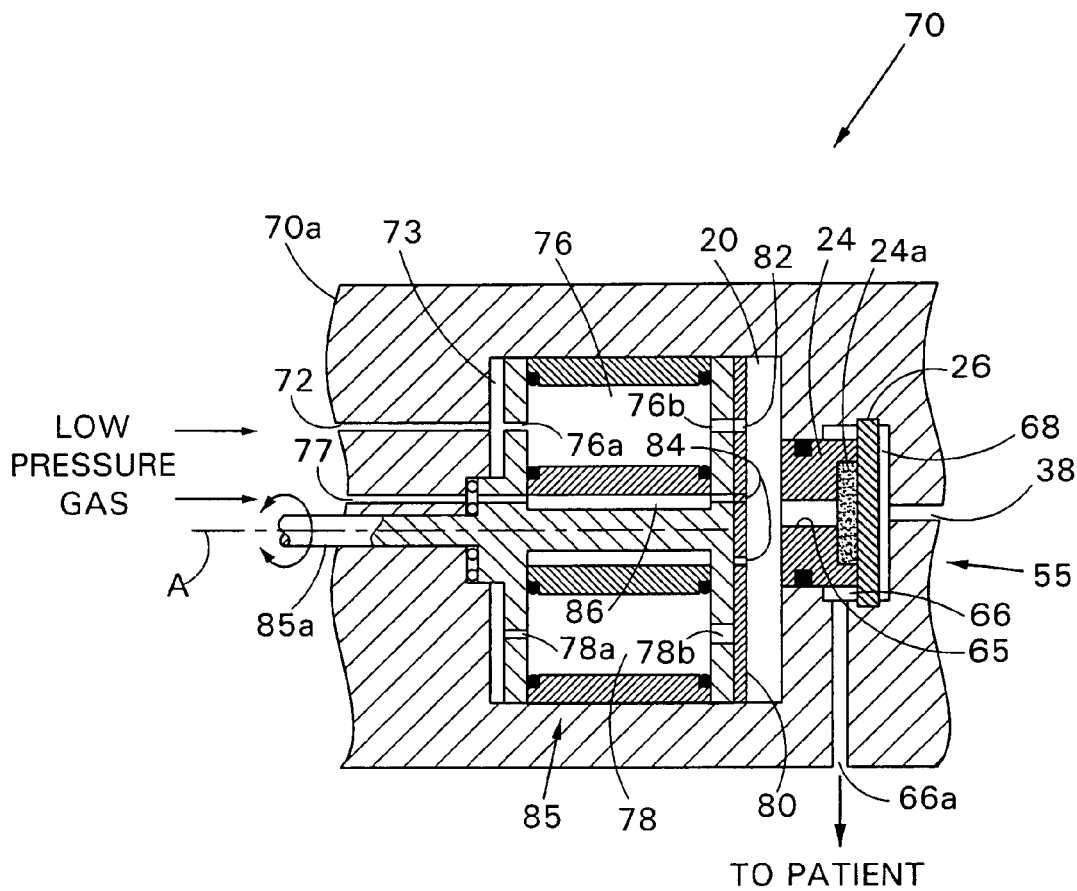
FIG. 7 is a partial side-sectional schematic of another multiple bolus regulator.
Figure 8:
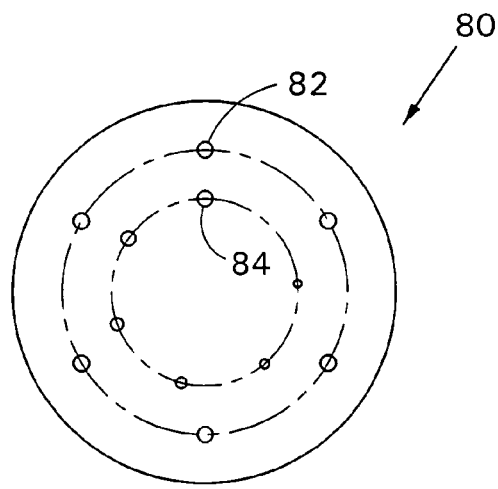
FIG. 8 is a plan view of a particular selector plate for use with the regulator of FIG. 7.

FIG. 7 is a partial side-sectional schematic of another multiple bolus regulator. The illustrated gas conserving regulator 70 differs from the regulator 100 (FIG. 5) in that the auxiliary bolus chambers 76, 78 are positioned within a housing 70a to receive gas from a supply passage 72 via a supply chamber 73 and upstream fill openings 76a, 78a, and are rotated about axis A by the shaft 85a of the selector device 85. Rotation of the auxiliary bolus chambers 76, 78 allows alignment of the openings 76b, 78b with the desired locations of a fixed plate 80 (FIG. 8). In FIG. 7, the opening 76b is aligned with a bolus circuit orifice 82 of the fixed plate 80 thereby connecting the bolus chamber 76 with the gas reservoir or common bolus chamber 20. The opening 78b of the auxiliary bolus chamber 78 is shown blocked, thereby isolating the chamber 78 from the gas reservoir 20 and the other auxiliary bolus chamber 76. In addition, continuous flow passages 77, 86 are blocked.

In operation, after the bolus gas is delivered, the tail gas flow is delivered into the gas reservoir 20 through supply passage 72, supply chamber 73, upstream opening 76a, first auxiliary bolus chamber 76, opening 76b, and bolus circuit orifice 82. In cases where the second auxiliary bolus chamber 78 is in use, gas will be passed through it in a similar manner.

As a result, the same fixed flow orifice that provides the tail flow also fills the bolus chamber(s). If multiple auxiliary bolus chambers are to be used, this will provide a tail flow made up of flow rates that come through multiple passages. The number of passages used corresponds to the number of auxiliary bolus chambers in use. Each passage that fills the auxiliary bolus chamber (and provides tail flow) can flow at the same flow rate (for example, 400 sccm). When more chambers (and thus more passages) are in use, the passages work in conjunction to provide the required tail flow.

For example, a knob setting of 1 LPM could provide flow from one auxiliary bolus chamber plus 400 sccm of tail flow. A setting of 2 LPM would provide flow from two auxiliary bolus chambers plus 800 sccm of tail flow (two orifices each providing 400 sccm).

The regulator 70 can also provide continuous flow to the patient. In such a case, the auxiliary bolus chambers can be blocked and a continuous flow circuit orifice 84 in plate 80 be aligned with the continuous flow passage 77. In this mode, the piloting mechanism can be disabled, so that there is a constant flow. If desired, the auxiliary bolus chambers can be used with a constant flow passing through both the continuous flow circuit and the bolus chambers to add extra flow such as for a tail flow.

FIG. 8 is a plain view of a particular selector plate for use with the regulator of FIG. 7. As shown, the selector plate 80 is shown with six pairs of orifices. The bolus circuit orifices 82 are on the outer diameter and the continuous circuit orifices 84 are on the inner diameter. The selector plate 80 would therefore control six auxiliary bolus chambers. The auxiliary bolus chambers would be annularly spaced at 60° intervals around the axis A (FIG. 7). The plate orifices 82, 84 are annularly spaced at something other than 60°, such as at 55° intervals around the axis A. It should be understood that the orifices 84 can be of different sizes to provide different flow rates, but that is not necessary.

While this invention has been particularly shown and described with references to particular embodiments thereof, it will be understood by those skilled in the art that various changes in form and details may be made therein without departing from the scope of the invention encompassed by the appended claims. For example, various features of the embodiments described and shown can be omitted or combined with each other. For example, the volume of a timing gas chamber can be adjustable and further include an adjustable flow rate therein, such as with an adjustable orifice member. Furthermore, although particular volumes, sizes and rates have been described, it is understood that such values can vary depending upon the application at hand.

Although the delivery of oxygen with the present invention is most common, the delivery of other therapeutic gases are contemplated, for example, nitrous oxide. In addition, the present invention can be employed for non-therapeutic uses, such as for the delivery of lethal gases, or for delivering other gases for industrial uses.

What is claimed is:

1. A medical gas conserving device for delivery a fixed volume of medical gas to a patient in response to an inhalation, comprising:
    a timing gas chamber for storing a user-adjustable volume of gas up to a first pressure;
    a vent to exhaust the gas stored in the timing gas chamber to atmosphere;
    a pilot valve disposed between the timing gas chamber and the vent, the pilot valve biased in a closed position to inhibit gas flow from the timing gas chamber to the vent, the pilot valve in gas communication with a patient via a passage such that a vacuum in the passage opens the pilot valve to allow gas flow from the timing gas chamber to the vent; and
    a slave valve disposed between a regulated supply of medical gas and a delivery passage to the patient, the slave valve in gas communication with the timing gas chamber such that when gas in the timing gas chamber is at the first pressure the slave valve is in a closed position to inhibit the flow of medical gas from the regulated supply to the delivery passage, and when gas in the timing gas chamber is below the first pressure the slave valve is in an opened position to allow medical gas to flow from the regulated supply to the delivery passage.

2. The device of claim 1 wherein the timing gas chamber includes a moveable piston acting as a wall of the timing gas chamber, the moveable piston being positionable by a user to adjust the volume of the timing gas chamber.

3. The device of claim 1 wherein the first pressure is determined by the area of an orifice.

4. The device of claim 3 wherein the orifice is selected from a plurality of orifices, each orifice having a respective area.

5. The device of claim 1 wherein the delivery valve member is a flexible membrane.

6. A method of manufacturing a medical gas conserving device for delivery a fixed volume of medical gas to a patient in response to an inhalation, comprising:
    forming a timing gas chamber for storing a user-adjustable volume of gas up to a first pressure;
    forming a vent to exhaust the gas stored in the timing gas chamber to atmosphere;
    disposing a pilot valve between the timing gas chamber and the vent, the pilot valve being biased in a closed position to inhibit gas flow from the timing gas chamber to the vent, the pilot valve in gas communication with a patient passage such that a vacuum in the passage opens the pilot valve to allow gas flow from the timing gas chamber to the vent; and
    disposing a slave valve between a regulated supply of medical gas and a delivery passage to the patient, the slave valve in gas communication with the timing gas chamber such that when gas in the timing gas chamber is at the first pressure the slave valve is in a closed position to inhibit the flow of medical gas from the regulated supply to the delivery passage, and when gas in the timing gas chamber is below the first pressure the slave valve is in an opened position to allow medical gas to flow from the regulated supply to the delivery passage.

7. The method of claim 6 wherein forming the timing gas chamber includes forming a moveable piston to act as a wall of the timing gas chamber, the moveable piston being positionable by a user to adjust the volume of the timing gas chamber.

8. The method of claim 6 further comprising forming an orifice having an area dimensioned to provide the first pressure.

9. The method of claim 8 wherein forming the orifice comprises fabricating a plurality of selectable orifices, each orifice having a respective area.

10. The method of claim 6 wherein the delivery valve member is a flexible membrane.

11. The device of claim 1 further comprising an adjustment system for providing the first pressure, the adjustment system including an orifice member having more than one orifice, each of a different size, which can be selectively positioned for selecting the flow rate of the gas into the timing gas chamber.

12. The method of claim 6 further comprising fabricating an adjustment system for providing the first pressure, the adjustment system including an orifice member having more than one orifice, each of a different size, which can be selectively positioned for selecting the flow rate of the gas into the timing gas chamber.

13. A medical gas conserving device for delivery a fixed volume of medical gas to a patient in response to an inhalation, comprising:
    a timing gas chamber for storing a user-adjustable volume of gas up to a first pressure, wherein the timing gas chamber includes a moveable piston acting as a wall of the timing gas chamber, the moveable piston being positionable by a user to adjust the volume of the timing gas chamber;
    a vent to exhaust the gas stored in the timing gas chamber to atmosphere;
    a pilot valve disposed between the timing gas chamber and the vent, the pilot valve biased in a closed position to inhibit gas flow from the timing gas chamber to the vent, the pilot valve in gas communication with a patient via a passage such that a vacuum in the passage opens the pilot valve to allow gas flow from the timing gas chamber to the vent; and a slave valve disposed between a regulated supply of medical gas and a delivery passage to the patient, the slave valve in gas communication with the timing gas chamber such that when gas in the timing gas chamber is at the first pressure the slave valve is in a closed position to inhibit the flow of medical gas from the regulated supply to the delivery passage, and when gas in the timing gas chamber is below the first pressure the slave valve is in an opened position to allow medical gas to flow from the regulated supply to the delivery passage.

14. The device of claim 13 wherein the first pressure is determined by the area of an orifice.

15. The device of claim 14 wherein the orifice is selected from a plurality of orifices, each orifice having a respective area.

16. The device of claim 13 wherein the delivery valve member is a flexible membrane.

17. The device of claim 13 further comprising an adjustment system for providing the first pressure, the adjustment system including an orifice member having more than one orifice, each of a different size, which can be selectively positioned for selecting the flow rate of the gas into the timing gas chamber.

18. A method of manufacturing a medical gas conserving device for delivery a fixed volume of medical gas to a patient in response to an inhalation, comprising:

forming a timing gas chamber for storing a user-adjustable volume of gas up to a first pressure including forming a moveable piston to act as a wall of the timing gas chamber, the moveable piston being positionable by a user to adjust the volume of the timing gas chamber;

forming a vent to exhaust the gas stored in the timing gas chamber to atmosphere;

disposing a pilot valve between the timing gas chamber and the vent, the pilot valve being biased in a closed position to inhibit gas flow from the timing gas chamber to the vent, the pilot valve in gas communication with a patient passage such that a vacuum in the passage opens the pilot valve to allow gas flow from the timing gas chamber to the vent; and disposing a slave valve between a regulated supply of medical gas and a delivery passage to the patient, the slave valve in gas communication with the timing gas chamber such that when gas in the timing gas chamber is at the first pressure the slave valve is in a closed position to inhibit the flow of medical gas from the regulated supply to the delivery passage, and when gas in the timing gas chamber is below the first pressure the slave valve is in an opened position to allow medical gas to flow from the regulated supply to the delivery passage.

19. The method of claim 18 further comprising forming an orifice having an area dimensioned to provide the first pressure.

20. The method of claim 19 wherein forming the orifice comprises fabricating a plurality of selectable orifices, each orifice having a respective area.

21. The method of claim 18 wherein the delivery valve member is a flexible membrane.

22. The method of claim 18 further comprising fabricating an adjustment system for providing the first pressure, the adjustment system including an orifice member having more than one orifice, each of a different size, which can be selectively positioned for selecting the flow rate of the gas into the timing gas chamber.

* * * * *